(12) United States Patent
Itsuki et al.

(10) Patent No.: US 6,310,228 B1
(45) Date of Patent: Oct. 30, 2001

(54) ORGANIC COPPER COMPOUND, LIQUID MIXTURE CONTAINING THE COMPOUND, AND COPPER THIN-FILM PREPARED USING THE SOLUTION

(75) Inventors: Atsushi Itsuki; Katsumi Ogi, both of Ohmiya (JP)

(73) Assignee: Mitsubishi Materials Corporation, Tokyo (JP)

( * ) Notice: Subject to any disclaimer, the term of this patent is extended or adjusted under 35 U.S.C. 154(b) by 0 days.

(21) Appl. No.: 09/736,305

(22) Filed: Dec. 15, 2000

(30) Foreign Application Priority Data

| Dec. 15, 1999 | (JP) | 11-355988 |
| Apr. 19, 2000 | (JP) | 12-118258 |
| Jul. 5, 2000 | (JP) | 12-203310 |
| Aug. 18, 2000 | (JP) | 12-248453 |
| Oct. 2, 2000 | (JP) | 12-302405 |

(51) Int. Cl.$^7$ .................................................. C07F 7/24
(52) U.S. Cl. ........................ 556/9; 556/11; 428/457; 427/250; 427/252; 106/1.05; 106/1.23; 106/1.26
(58) Field of Search .................. 556/9, 12; 428/457; 427/250, 252; 106/1.05, 1.26, 1.23

(56) References Cited

U.S. PATENT DOCUMENTS

| 5,767,301 | * | 6/1998 | Senzaki et al. | 556/9 |
| 6,090,960 | * | 7/2000 | Senzaki et al. | 556/9 |
| 6,130,345 | * | 10/2000 | Doppelt | 556/12 |
| 6,184,403 | * | 2/2001 | Welch et al. | 556/12 |

* cited by examiner

Primary Examiner—Paul F. Shaver
(74) Attorney, Agent, or Firm—Oblon, Spivak, McClelland, Maier & Neustadt, P.C.

(57) ABSTRACT

An organic copper compound is provided that is represented by the following formula (1) in which monovalent copper is coordinated with a β-diketone compound and an unsaturated hydrocarbon compound having a silyloxy group:

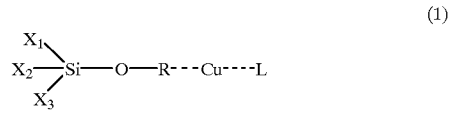

(1)

wherein R Is an unsaturated hydrocarbon moiety, L is the β-diketone compound, $X_1$, $X_2$, and $X_3$ are each a hydrogen atom, an alkyl group having 1 to 5 carbon atoms, or an alkoxy group having 1 to 4 carbon atoms, and $X_1$, $X_2$, and $X_3$ may be the same or different from each other. The organic copper compound is barely decomposed in a stock solution before use, has a prolonged storage life, exhibits a high film deposition rate, can be effectively decomposed on a substrate, is highly volatile, and exhibits high adhesiveness to an underlayer.

62 Claims, No Drawings

ORGANIC COPPER COMPOUND, LIQUID MIXTURE CONTAINING THE COMPOUND, AND COPPER THIN-FILM PREPARED USING THE SOLUTION

BACKGROUND OF THE INVENTION

1. Field of the Invention

The present invention relates to organic copper compounds for making copper (Cu) thin-films used in wiring of semiconductor devices by a metal organic chemical vapor deposition (hereinafter referred to as MOCVD) process, to liquid mixtures (solutions) containing the compounds, and to copper thin-films prepared by the MOCVD process using the solutions.

2. Description of the Related Art

As an organic copper compound used in a MOCVD process, copper complex Cu(I) tmvs·hfac (wherein tmvs represents trimethylvinylsilane and hfac represents hexafluoroacetylacetonate), which satisfies a combination of strict chemical, structural, and electrical requirements over a relatively wide range, has selective deposition ability, and is liquid at room temperature, is well known in Japanese Unexamined Patent Application Publication No. 5-202,476. This compound, however, is extremely unstable, and is readily decomposed at room temperature to precipitate metallic copper and to form copper(II)(hfac)$_2$ as a by-product. Thus, the organic copper compound cannot be uniformly supplied during a film deposition process, resulting in less reproducible film deposition.

In order to solve this problem, copper(I) atms·hfac (wherein atms represents allyltrimethylsilane), which exhibits a more stable vaporization rate than that of copper(I) tmvs·hfac, high volatility, and high thermal stability, and is liquid at room temperature, is disclosed in Japanese Unexamined Patent Application Publication Nos. 7-252266 and 10-131514.

On the other hand, a copper precursor compound is disclosed in Japanese Unexamined Patent Application Publication No. 10-195654. This compound contains copper(I) hfac and methoxymethylsilylolefin ligand. When the compound is heated to a vaporization temperature, the electron donor ability of oxygen in the methoxymethylsilylolefin ligand provides a stable bond between the copper and the methoxymethylsilylolefin ligand. In this copper precursor compound, the oxygen atom of the methoxy group primarily suppresses the volatility of the copper precursor compound. Thus, the copper precursor compound exhibits improved thermal stability and a prolonged life.

Both copper(I) atms·hfac disclosed in Japanese Unexamined Patent Application Publication Nos. 7-252266 and 10-135154 and the copper precursor compound disclosed in Japanese Unexamined Patent Application Publication No. 195654, as well as copper(I) tmvs·hfac, exhibit low film deposition rate and poor adhesiveness to underlayers compared to physical deposition processes, such as a sputtering process.

SUMMARY OF THE INVENTION

The present invention provides a copper based organic compound which can exhibit a high film deposition rate, can effectively decompose on a substrate, is highly volatile, and exhibits high adhesiveness to an underlayer. The present invention also provides a liquid mixture containing this compound. The organic compound barely decomposes during storage and has a prolonged life. The organic compound can be used to form a high-purity copper thin film that firmly adheres to an underlayer.

A first aspect of the present invention relates to an organic copper compound represented by the following formula (1) in which monovalent copper is coordinated with a β-diketone compound and an unsaturated hydrocarbon compound having a silyloxy group:

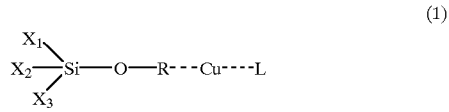

In the formula, R is an unsaturated hydrocarbon moiety, L is the β-diketone compound, $X_1$, $X_2$, and $X_3$ are each a hydrogen atom, an alkyl group having 1 to 5 carbon atoms, or an alkoxy group having 1 to 4 carbon atoms, and $X_1$, $X_2$, and $X_3$ may be the same or different from each other.

The organic copper compound according to the first aspect has an oxosilane group in which a silicon atom having electron donor ability is directly bonded to an oxygen atom having higher electron donor ability. By using the oxosilane group as a ligand, the π bonding of the copper atom is enhanced, and the chemical stability of the copper compound is improved.

A second aspect of the present invention relates to an organic copper compound represented by the following formula (2) in which monovalent copper is coordinated with hexafluoroacetylacetone and an olefinic hydrocarbon compound with 3 or more carbon atoms having a silyloxy group bonded to one or two alkoxy groups. In this organic copper compound, monovalent copper is coordinated with hexafluoroacetylacetone as the β-diketone compound and the unsaturated hydrocarbon compound having the silyloxy group.

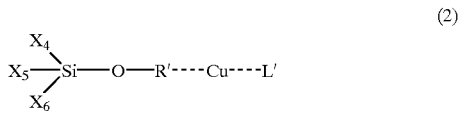

In the formula, R' is an olefinic hydrocarbon moiety with 3 or more carbon atoms, L' is the hexafluoroacetylacetone, one or two of $X_4$, $X_5$, and $X_6$ are each an alkoxy group having 1 to 8 carbon atoms, the others of $X_4$, $X_5$, and $X_6$ are each an alkyl group having 1 to 8 carbon atoms or a hydrogen atom, and the alkoxy groups or the alkyl groups may be the same or different from each other.

Preferably, the olefinic hydrocarbon moiety is propenyl, butenyl, or pentenyl.

In the organic copper compound according to the second aspect, a combination of the alkoxy group and the alkyl group yields electron donor ability over the alkoxy group and the olefin moiety. The organic copper compound represented by the formula (2) is barely decomposed in a stock solution and exhibits high stability. In the compound represented by the formula (2), the alkyl group and the alkoxy group results in high steric hindrance. Thus, the compound has a high film deposition rate, is effectively decomposed on a substrate, is highly volatile, and exhibits high adhesiveness to an underlayer.

A third aspect of the present invention relates to an organic copper compound represented by the following formula (3) in which monovalent copper is coordinated with hexafluoroacetylacetone and an olefinic hydrocarbon compound with 4 or more carbon atoms having a silyloxy group bonded to three alkoxy groups:

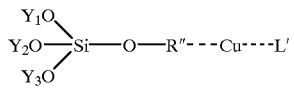
(3)

In the formula, R" is an olefinic hydrocarbon moiety with 4 or more carbon atoms, L' is the hexafluoroacetylacetone, $Y_1$, $Y_2$, and $Y_3$ are each an alkoxy group having 1 to 4 carbon atoms, and $Y_1$, $Y_2$, and $Y_3$ may be the same or different from each other.

Preferably, the olefinic hydrocarbon moiety is propenyl, butenyl, or pentenyl.

In the organic copper compound according to the second aspect, all the groups other than the olefinic hydrocarbon moiety bonded to the silicon atom are alkoxy groups. Thus, the electronic flow is further enhanced in view of molecular structure. Thus, copper readily approaches a substrate used in a deposition process, and the film deposition rate is increased.

A fourth aspect of the present invention relates to a liquid mixture comprising the organic copper compound according to any one of the first to third aspect and at least one liquid compound selected from the group consisting of trimethylvinylsilane, vinyloxytrimethylsilane, allyloxytrimethylsilane, allyltrimethylsilane, 3-hexyne, 2-butyne, and a Cu(I) hexafluoroacetylacetonate compound coordinated therewith.

This liquid mixture exhibits a higher deposition rate in a MOCVD process compared to that of a solution not containing the liquid compound.

A fifth aspect of the present invention relates to a liquid mixture comprising the organic copper compound according to any one of the first to third aspect and at least one liquid compound selected from the group consisting of copper(I) allyltrimethylsilane hexafluoroacetylacetonate (hereinafter referred to as copper(I) atms·hfac) represented by the following formula (4), copper(I) trimethylvinylsilane hexafluoroacetylacetonate (hereinafter referred to as copper(I) tmvs·hfac) represented by the following formula (5), and copper(I) trimethoxyvinylsilane hexafluoroacetylacetonate (hereinafter referred to as copper(I) tmovs·hfac) represented by the following formula (6).

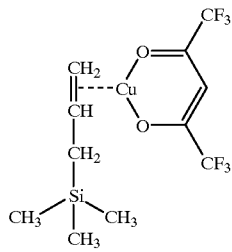
(4)

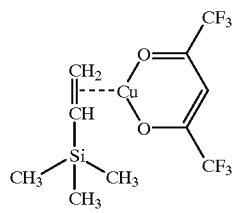
(5)

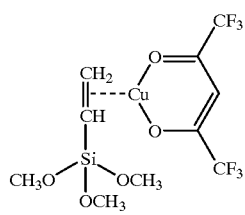
(6)

In the fifth aspect of the present invention, the organic copper compound according to one of the first to third aspects is mixed with the above liquid compound, and a copper thin film is formed using the mixture by a MOCVD process. Thus, the copper(I) complex is readily decomposed in an initial stage of the process, and copper is rapidly deposited on an underlayer at the initial stage, resulting in a high deposition rate of the copper thin film.

A sixth aspect of the present invention relates to a liquid mixture comprising the liquid mixture according to the fifth aspect and at least one compound selected from the group consisting of allyltrimethylsilane (hereinafter referred to as atms), allyltrimethoxysilane (hereinafter referred to as atmos), trimethylvinylsilane (hereinafter referred to as tmvs), and trimethoxyvinylsilane (hereinafter referred to as tmovs).

In the sixth aspect, at least one compound selected from atms, atmos, tmvs, and tmovs is added. Thus, the proportion of carbon double bonds in atoms etc. is increased in the solution and π bonding of copper is enhanced. As a result, the organic copper compound is barely decomposed in a stock solution and has a prolonged storage life.

DETAILED DESCRIPTION OF THE PREFERRED EMBODIMENTS

The organic copper compound of the present invention is a compound represented by the above formula (1) in which monovalent copper is coordinated with a β-diketone compound and an unsaturated hydrocarbon compound having a silyloxy group; a compound represented by the above formula (2) in which monovalent copper is coordinated with hexafluoroacetylacetone and an olefinic hydrocarbon compound with 3 or more carbon atoms having a silyloxy group bonded to one or two alkoxy groups; or a compound represented by the above formula (3) in which monovalent copper is coordinated with hexafluoroacetylacetone and an olefinic hydrocarbon compound with 4 or more carbon atoms having a silyloxy group bonded to three alkoxy groups.

In the silyloxy group represented by the formula (1), $X_1$, $X_2$ and $X_3$ are each a hydrogen atom, an alkyl group having 1 to 5 carbon atoms, or an alkoxy group having 1 to 4 carbon atoms, and $X_1$, $X_2$, and $X_3$ may be the same or different from each other.

Examples of the β-diketone compounds are hexafluoroacetylacetone and 1,3-dihydroxy-1,3-propanedione. These β-diketone compounds are considered to be coordinated to monovalent copper as shown in the following formula (7) or (8).

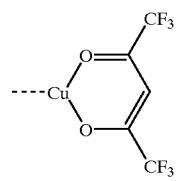

(7)

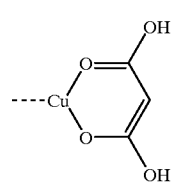

(8)

Examples of the unsaturated hydrocarbon compounds are olefinic hydrocarbon compounds having alkenyl groups, e.g., ethenyl, propenyl, butenyl, and pentenyl groups, and acetylenic hydrocarbon compounds having alkynyl groups, e.g., ethynyl, propynyl, butynyl, pentynyl, and hexynyl groups.

The liquid mixture of the present invention may be prepared by mixing only the organic copper compound represented by the above formula (2) or mixing this organic copper compound with another organic copper compound containing monovalent copper.

A stock solution for forming a copper thin film by metal organic chemical vapor deposition of the present invention is prepared by mixing the organic copper compound liquid mixture with at least one liquid compound selected from atms, atmos, tmvs, and tmovs.

Table 1 shows combinations of the alkenyl group and the silyloxy group bonded thereto in the present invention. These combinations are applicable to both cases in which the β-diketone compounds are hexafluoroacetylacetone and 1,3-dihydroxy-1,3-propanedione.

TABLE 1

| | | Type of Silyloxy Group | | |
|---|---|---|---|---|
| No. | Type of Alkenyl Group | $X_1$ | $X_2$ | $X_3$ |
| 1 | $CH_2=CH-$ | Methyl | Methyl | Methyl |
| 2 | $CH_2=CH-CH_2-$ | Methyl | Methyl | Methyl |
| 3 | $CH_2=CH-$ | t-Butyl | t-Butyl | t-Butyl |
| 4 | $CH_2=CH-$ | Methoxy | n-Butyl | n-Butyl |
| 5 | $CH_2=CH-CH-$ | Ethoxy | Ethoxy | Ethoxy |
| 6 | $CH_2=CH-CH_2-$ | i-Butyl | i-Butyl | i-Butyl |
| 7 | $CH_3-CH=CH-CH_2-$ | Propyl | Propyl | Propyl |
| 8 | $CH_3-CH_2-CH=CH-$ | Methoxy | Methyl | Methyl |
| 9 | $CH_3-CH_2-CH_2-CH=CH-$ | Methyl | Methyl | Methyl |
| 10 | $CH_3-CH_2-CH=CH-CH_2-$ | Methoxy | Methyl | Methyl |
| 11 | $CH_2=CH-$ | Pentyl | Pentyl | Pentyl |
| 12 | $CH_2=CH-CH_2-$ | Methyl | i-Pentyl | i-Pentyl |
| 13 | $CH_2=CH-$ | Methyl | Methyl | i-Pentyl |
| 14 | $CH_2=CH-$ | t-Pentyl | t-Pentyl | t-Pentyl |
| 15 | $CH_2=CH-CH_2-$ | Ethyl | t-Pentyl | t-Pentyl |
| 16 | $CH_2=CH-CH_2-$ | Methyl | t-Pentyl | t-Pentyl |
| 17 | $CH_3-CH=CH-CH_2-$ | t-Pentyl | t-Pentyl | t-Pentyl |
| 18 | $CH_3-CH=CH-CH_2-$ | t-Butyl | i-Pentyl | i-Pentyl |
| 19 | $CH_2=CH-CH_2-$ | Ethoxy | i-Pentyl | i-Pentyl |
| 20 | $CH_2=CH-CH_2-$ | Ethoxy | t-Pentyl | t-Pentyl |
| 21 | $CH_3-CH_2-CH=CH-CH_2-$ | Hydrogen | Hydrogen | Hydrogen |

TABLE 1-continued

| | | Type of Silyloxy Group | | |
|---|---|---|---|---|
| No. | Type of Alkenyl Group | $X_1$ | $X_2$ | $X_3$ |
| 22 | $CH_3-CH_2-CH=CH-CH_2-$ | Hydrogen | Hydrogen | Methyl |
| 23 | $CH_3-CH_2-CH=CH-CH_2-$ | Hydrogen | Methyl | Methyl |
| 24 | $CH_3-CH_2-CH=CH-CH_2-$ | Hydrogen | Ethyl | Ethyl |
| 25 | $CH_3-CH_2-CH=CH-CH_2-$ | Hydrogen | i-Propyl | i-Propyl |
| 26 | $CH_3-CH_2-CH=CH-CH_2-$ | Hydrogen | i-Butyl | i-Butyl |
| 27 | $CH_3-CH_2-CH=CH-CH_2-$ | Hydrogen | t-Butyl | t-Butyl |
| 28 | $CH_3-CH_2-CH=CH-CH_2-$ | Hydrogen | i-Pentyl | i-Pentyl |
| 29 | $CH_3-CH_2-CH=CH-CH_2-$ | Hydrogen | t-Pentyl | t-Pentyl |
| 30 | $CH_3-CH_2-CH=CH-CH_2-$ | Hydrogen | Ethoxy | Ethoxy |

(n-: normal-, i-: iso-, t-: tertiary-)

Tables 2 and 3 show combinations of the alkynyl group and the silyloxy group bonded thereto of the present invention. These combination are applicable to both cases in which the β-diketone compound are hexafluoroacetylacetone and 1,3-dihydroxy-1,3-propanedione

TABLE 2

| | | Type of Silyloxy Group | | |
|---|---|---|---|---|
| No. | Type of Alkynyl Group | $X_1$ | $X_2$ | $X_3$ |
| 31 | $CH≡C-$ | Methyl | Methyl | Methyl |
| 32 | $CH≡C-$ | Methoxy | Methyl | Methyl |
| 33 | $CH≡C-$ | Hydrogen | t-Butyl | t-Butyl |
| 34 | $CH≡C-$ | Methoxy | n-Butyl | n-Butyl |
| 35 | $CH≡C-$ | t-Butyl | t-Butyl | t-Butyl |
| 36 | $CH≡C-$ | Ethoxy | Ethoxy | Ethoxy |
| 37 | $CH≡C-$ | Ethyl | Ethyl | Ethyl |
| 38 | $CH_3-C≡C-$ | Methyl | Methyl | Methyl |
| 39 | $CH_3-C≡C-$ | Propyl | Propyl | Propyl |
| 40 | $CH_3-C≡C-$ | i-Butyl | i-Butyl | i-Butyl |
| 41 | $CH≡C-$ | Pentyl | Pentyl | Pentyl |
| 42 | $CH≡C-$ | Methyl | i-Pentyl | i-Pentyl |
| 43 | $CH≡C-$ | Methyl | Methyl | i-Pentyl |
| 44 | $CH≡C-$ | t-Pentyl | t-Pentyl | t-Pentyl |
| 45 | $CH≡C-$ | Methyl | t-Pentyl | t-Pentyl |
| 46 | $CH≡C-$ | Ethyl | t-Pentyl | t-Pentyl |
| 47 | $CH≡C-$ | t-Butyl | t-Pentyl | t-Pentyl |
| 48 | $CH≡C-$ | t-Butyl | i-Pentyl | i-Pentyl |
| 49 | $CH≡C-$ | Ethoxy | i-Pentyl | i-Pentyl |
| 50 | $CH≡C-$ | Ethoxy | i-Pentyl | t-Pentyl |

(n-: normal-, i-: iso-, t-: tertiary-)

TABLE 3

| | | Type of Silyloxy Group | | |
|---|---|---|---|---|
| No. | Type of Alkynyl Group | $X_1$ | $X_2$ | $X_3$ |
| 51 | $CH_3-C≡C-$ | Propyl | Propyl | Propyl |
| 52 | $CH≡C-CH_2-$ | Methyl | Methyl | Methyl |
| 53 | $CH≡C-CH_2-$ | Ethyl | Ethyl | Ethyl |
| 54 | $CH_3-C≡C-CH_2-$ | i-Butyl | i-Butyl | i-Butyl |
| 55 | $CH_3-C≡C-CH_2-$ | Methoxy | Methyl | Methyl |
| 56 | $CH_3-C≡C-CH_2-$ | Methyl | Methyl | Methyl |
| 57 | $CH_3-CH_2-C≡C-$ | Methoxy | Methyl | Methyl |
| 58 | $CH_3-CH_2-C≡C-$ | i-Butyl | i-Butyl | i-Butyl |
| 59 | $CH_3-CH_2-C≡C-$ | Propyl | Propyl | Propyl |
| 60 | $CH_3-CH_2-C≡C-$ | Methyl | Methyl | Methyl |
| 61 | $CH≡C-$ | Hydrogen | Hydrogen | Hydrogen |
| 62 | $CH≡C-$ | Hydrogen | Hydrogen | Methyl |
| 63 | $CH≡C-$ | Hydrogen | Methyl | Methyl |
| 64 | $CH≡C-$ | Hydrogen | Hydrogen | Ethoxy |
| 65 | $CH≡C-$ | Hydrogen | i-Pentyl | i-Pentyl |
| 66 | $CH≡C-$ | Hydrogen | t-Pentyl | t-Pentyl |
| 67 | $CH_3-C≡C-CH_2-$ | Hydrogen | i-Pentyl | i-Pentyl |
| 68 | $CH_3-C≡C-CH_2-$ | Hydrogen | t-Pentyl | t-Pentyl |

TABLE 3-continued

| | | Type of Silyloxy Group | | |
|---|---|---|---|---|
| No. | Type of Alkynyl Group | $X_1$ | $X_2$ | $X_3$ |
| 69 | $CH_3$—$CH_2$—C≡C— | Hydrogen | i-Pentyl | i-Pentyl |
| 70 | $CH_3$—$CH_2$—C≡C— | Hydrogen | t-Pentyl | t-Pentyl |

(i-: iso-, t-: tertiary-)

The organic copper compound 1 and 2 show in Table 1 will now be described in detail.

The organic copper compound 1 in Table 1 is copper(I) vinyloxytrimethylsilane hexafluoroacetylacetonate (hereinafter abbreviated as copper(I) votms·hfac), which is represented by the following formula 9. The organic copper compound 2 in Table 1 is copper(I) allyloxytrimethylsilane hexafluroacetylacetonate (hereinafter abbreviated as copper (I) aotms·hfac), which is represented by the following formula 10.

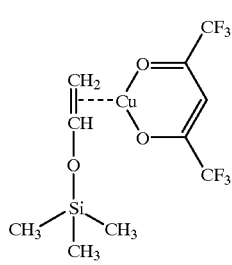

(9)

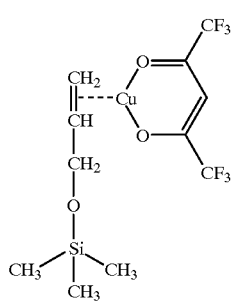

(10)

The organic copper compound represented as the copper (I) vinyloxytrimethylsilalne hexafluroacetyacetonate in this specification is formally represented as copper(I) (oxytrimethylsilylethene) (1,1,1,5,5,5-hexafluoro-2,4-pentanedionate). The organic copper compound represented as the copper(I) allyloxytrimethylsilane hexafluoroacetylacetonate is formally represented as copper(I) (oxyrrimethylsilylpropene)(1,1,1,5,5,5-hexafluoro-2,4-pentanedionate.

Although a stock solution for metal organic chemical vapor deposition can be prepared using only the organic copper compound of the present invention, a liquid mixture is preferably prepared using the organic copper compound of the present invention and any known copper(I) complex, because the deposition rate of the copper thin film is increased compared to the single use of one of these compounds. Examples of such copper(I) complexes are copper (I) hexafluoroacetylacetonate coordinated with trimethylvinylsilane, vinyloxytrimethylsilane, allyloxytrimethylsilane, allyltrimethylsilane, 3-hexyne, or 2-butyne. When the above tmvs, atms, or trimethoxyvinylsilane (tmovs) is added alone, the deposition rate of the copper thin film is also increased.

The use of the above mixed liquid compound further enhances the stability of the organic copper compound, and the stabilized stock solution can be fed into an evaporation chamber or a deposition chamber. As a result, the deposition rate of the copper thin film is increased in MOCVD. In particular, the addition of copper(I) hexafluoroacetylacetonate coordinated with trimethylvinylsilane or the like facilitates the generation of nuclei on a substrate and promotes the deposition of the copper thin film.

In the organic copper compound represented by the formula (2), R' is an olefinic hydrocarbon moiety with 3 or more carbon atoms, L' is the hexafluoroacetylacetone, one or two of $X_4$, $X_5$, and $X_6$ are each an alkoxy group having 1 to 8 carbon atoms, the others of $X_4$, $X_5$, and $X_6$ are each an alkyl group having 1 to 8 carbon atoms or a hydrogen atom, and the alkoxy groups or the alkyl groups may be the same or different from each other. Table 4 shows examples of the organic copper compounds.

TABLE 4

| No. | Olefinic Hydrocarbon Compound | $X_4$ | $X_5$ | $X_6$ |
|---|---|---|---|---|
| 201 | $CH_2$=CH—$CH_2$—Si(—$X_4$)(—$X_5$)(—$X_6$) | $CH_3O$ | $CH_3$ | $CH_3$ |
| 202 | $CH_2$=CH—$CH_2$—Si(—$X_4$)(—$X_5$)(—$X_6$) | $C_2H_5O$ | $C_2H_5O$ | $CH_3$ |
| 203 | $CH_2$=CH—$CH_2$—Si(—$X_4$)(—$X_5$)(—$X_6$) | $C_3H_7O$ | $C_3H_7O$ | $CH_3$ |
| 204 | $CH_2$=CH—$CH_2$—Si(—$X_4$)(—$X_5$)(—$X_6$) | $C_4H_9O$ | $C_4H_9O$ | $CH_3$ |
| 205 | $CH_2$=CH—$CH_2$—$CH_2$—Si(—$X_4$)(—$X_5$)(—$X_6$) | $CH_3O$ | $CH_3O$ | $CH_3$ |
| 206 | $CH_2$=CH—$CH_2$—$CH_2$—Si(—$X_4$)(—$X_5$)(—$X_6$) | $C_2H_5O$ | $C_2H_5O$ | $CH_3$ |
| 207 | $CH_3$—CH=CH—$CH_2$—Si(—$X_4$)(—$X_5$)(—$X_6$) | $C_3H_7O$ | $C_3H_7O$ | $CH_3$ |
| 208 | $CH_3$—CH=CH—$CH_2$—Si(—$X_4$)(—$X_5$)(—$X_6$) | $C_4H_9O$ | $C_4H_9O$ | $CH_3$ |
| 209 | $CH_2$=CH—$CH_2$-$CH_2$-$CH_2$—Si(—$X_4$)(—$X_5$)(—$X_6$) | $CH_3O$ | $CH_3O$ | $CH_3$ |

TABLE 4-continued

| No. | Olefinic Hydrocarbon Compound | $X_4$ | $X_5$ | $X_6$ |
|---|---|---|---|---|
| 210 | CH₂=CH—CH(CH₃)—CH₂—Si(X₄)(X₅)(X₆) | $C_2H_5O$ | $C_2H_5O$ | $CH_3$ |
| 211 | CH₃—CH=CH—CH₂—CH₂—Si(X₄)(X₅)(X₆) | $C_3H_7O$ | $C_3H_7O$ | $CH_3$ |
| 212 | CH₃—CH₂—CH=CH—CH₂—Si(X₄)(X₅)(X₆) | $C_4H_9O$ | $C_4H_9O$ | $CH_3$ |

In the organic copper compound represented by the formula (3), R″ is an olefinic hydrocarbon moiety with 4 or more carbon atoms, L′ is the hexafluoroacetylacetone, $Y_1$, $Y_2$, and $Y_3$ are each an alkoxy group having 1 to 4 carbon atoms, and $Y_1$, $Y_2$, and $Y_3$ may be the same or different from each other. Table 5 shows examples of the organic copper compounds.

TABLE 5

| No | Olefinic Hydrocarbon Compounds | $Y_1$ | $Y_2$ | $Y_3$ |
|---|---|---|---|---|
| 213 | CH₂=CH—CH₂—CH₂—Si(OY₁)(OY₂)(OY₃) | $CH_3$ | $CH_3$ | $CH_3$ |
| 214 | CH₂=CH—CH₂—CH₂—Si(OY₁)(OY₂)(OY₃) | $C_2H_5$ | $C_2H_5$ | $C_2H_5$ |
| 215 | CH₂=CH—CH₂—CH₂—Si(OY₁)(OY₂)(OY₃) | $C_3H_7$ | $C_3H_7$ | $C_3H_7$ |
| 216 | CH₂=CH—CH₂—CH₂—Si(OY₁)(OY₂)(OY₃) | $C_4H_9$ | $C_4H_9$ | $C_4H_9$ |
| 217 | CH₃—CH—CH—CH₂—Si(OY₁)(OY₂)(OY₃) | $CH_3$ | $CH_3$ | $CH_3$ |
| 218 | CH₃—CH—CH—CH₂—Si(OY₁)(OY₂)(OY₃) | $C_2H_5$ | $C_2H_5$ | $C_2H_5$ |
| 219 | CH₃—CH—CH—CH₂—Si(OY₁)(OY₂)(OY₃) | $C_3H_7$ | $C_3H_7$ | $C_3H_7$ |
| 220 | CH₂=CH(CH₂)₃—Si(OY₁)(OY₂)(OY₃) | $CH_3$ | $CH_3$ | $CH_3$ |
| 221 | CH₂=CH(CH₂)₃—Si(OY₁)(OY₂)(OY₃) | $C_2H_5$ | $C_2H_5$ | $C_2H_5$ |
| 222 | CH₃—CH—CH(CH₂)₂—Si(OY₁)(OY₂)(OY₃) | $CH_3$ | $CH_3$ | $CH_3$ |
| 223 | CH₃—CH₂—CH=CH—CH₂—Si(OY₁)(OY₂)(OY₃) | $C_2H_5$ | $C_2H_5$ | $C_2H_5$ |
| 224 | CH₂=CH—CH(CH₃)—CH₂—CH₂—Si(OY₁)(OY₂)(OY₃) | $C_3H_7$ | $C_3H_7$ | $C_3H_7$ |

When the copper thin film is formed using a liquid mixture containing the organic copper compound represented by the formula (2) or (3) (hereinafter referred to as Compound A) and at least one liquid compound containing monovalent copper (hereinafter referred to as Compound B) selected from the group consisting of copper(I) allyltrimethylsilane hexafluoroacetylacetonate, copper(I) trimethylvinylsilane hexafluoroacetylacetonate, and copper(I) trimethoxyvinylsilane hexafluoroacetylacetonate by a MOCVD process, the stability of the organic copper compound is further enhanced, and the stabilized stock solution can be fed into an evaporation chamber or a deposition chamber. As a result, the deposition rate of the copper thin film is increased in MOCVD. Examples of the organic copper compounds containing monovalent copper are copper(I) atms·hfac represented by the formula (4), copper(I) tmvs·hfac represented by the formula (5), and copper(I) tmovs·hfac represented by the formula (6). In particular, the addition of copper(I) hexafluoroacetylacetonate coordinated with tmvs or the like facilitates the generation of nuclei on a substrate and promotes the deposition of the copper thin film.

When Compound B is mixed with Compound A, preferably 0.01 to 40 parts by weight, and more preferably 0.05 to 10 parts by weight, of Compound B is added to 100 parts by weight of Compound A. At a content of less than the lower limit of Compound B, the effect of the addition is not noticeable, and thus, the deposition rate of the copper thin film is not increased. At a content exceeding the upper limit of Compound B, the concentration of impurities in the copper thin film increases, resulting in deterioration of the quality of the thin film. Moreover, the deposition rate of the copper thin film is not very significantly increased at such a high concentration.

At least one compound (hereinafter referred to as Compound C) selected from the group consisting of atms, atmos, tmvs, and tmovs is preferably used together with Compound A and Compound B in the present invention. Compound C is added in an amount of preferably 0.01 to 40 parts by weight, and more preferably 0.05 to 10 parts by weight, to 100 parts by weight of Compound B. At a content of less than the lower limit of Compound C, the effect of the addition is not noticeable, and thus, the deposition rate of the copper thin film is not increased. At a content exceeding the upper limit of Compound C, the concentration of impurities in the copper thin film increases, resulting in deterioration of the quality of the thin film. Moreover the deposition rate of the copper thin film is not so significantly increased at such a high concentration.

Copper thin films prepared using organic copper compounds 1 to 70 shown in Tables 1 to 3 and organic copper compounds 201 to 224 shown in Tables 4 and 5 can firmly adhere to underlayers and have high purity. Such a copper thin film is formed by a MOCVD process, for example, on a TiN film or a TaN film, which is formed on a $SiO_2$ film on a silicon substrate by a sputtering process or a MOCVD process. The type of the substrate, however, is not limited in the present invention.

Examples of the present invention will now be described.

EXAMPLE 1

Synthesis and identification of copper(I) aotms·hfac represented by the above formula (10) will be described. Into 13.0 grams of copper(I) oxide, 150 ml of dried methylene chloride thoroughly deaerated using nitrogen was poured to form a suspension. While vigorously stirring the suspension, 5.32 g of vinyloxytrimethylsilane was added to the suspension, and then 12.6 g of 1,1,1,5,5,5-hexafluoro-2,4-pentanedione was added dropwise to the suspension from a dropping fimnel. The solution was stirred for 4 hours and was filtered in a nitrogen stream. The filtrate was evaporated at 35° C. under a reduced pressure to obtain a deep green liquid. The liquid was purified by column chromatography to obtain 10.5 g of a pale yellowish liquid organic copper compound, that is, copper(I) oxytrimethylsilylethene 1,1,1, 5,5,5-hexafluoro-2,4-pentanedionate. The resulting organic copper compound was identified by NMR and elemental analysts. In $^1$H-NMR ($CDCl_3$), peaks were observed at δ of 0.055 (s, 9H), 3.13 (m, 2H), 5.45 (m, 1H), and 6.08 (s, 1H).

According to the elemental analysis, the Cu content was 17.12% (theoretical: 17–18%) and the O content was 12.32% (theoretical: 12.31%).

Using a solution comprising the synthesized copper(I) aotms·hfac, copper thin films were formed by a MOCVD process. Using a silicon substrate provided with a TiN film with a thickness of 50 nm which was formed by a sputtering process on a $SiO_2$ film with a thickness of 5,000 Å on the substrate, the substrate temperature was changed to seven levels of 150° C., 160° C., 170° C., 180° C., 190° C., 200° C., and 210° C. The evaporation temperature was set at 70° C. and the pressure was set at 2 torr. Ar gas was used as a carrier gas and the flow rate was 100 sccm.

The stock solution for forming the copper thin film was supplied for 5 minutes at a rate of 0.2 cc/min., and the film thickness was observed by a cross-sectional scanning electron microscopic image. Table 6 shows the maximum film thickness per unit time. The specific resistance of the film was measured using a four-probe-type resistivity meter and the surface roughness of the film was measured by an electron-beam surface-roughness analyzer ERA-8000 (made by Elionix Inc.). The surface roughness is defined by the difference between the topmost portion and the bottommost portion on the surface. These results are also shown in Table 6.

EXAMPLE 2

Synthesis and identification of copper(I) votms·hfac represented by the above formula (9) will be described. Into 13.0 grams of copper(I) oxide, 150 ml of dried methylene chloride thoroughly deaerated using nitrogen was poured to form a suspension. While vigorously stirring the suspension, 6.92 g of allyloxytrimethylsilane was added to the suspension, and then 12.6 g of 1,1,1,5,5,5-hexafluoro-2,4-pentanedione was added dropwise to the suspension from a dropping funnel. The solution was stirred for 4 hours and was filtered in a nitrogen stream. The filtrate was evaporated at 35° C. under a reduced pressure to obtain a deep green liquid. The liquid was purified by column chromatography to obtain 10.5 g of a pale yellowish liquid organic copper compound, that is, copper(I) oxytrimethylsilylpropene 1,1, 1,5,5,5-hexafluoro-2,4-pentanedionate. The resulting organic copper compound was identified by NMR and elemental analysis. In $^1$H-NMR ($CDCl_3$), peaks were observed at δ of 0.061 (s, 9H), 1.62 (d, 2H, J=7.82 Hz), 4.13 (m, 2H), 5.46 (m, 1H), and 6.12 (s, 1H). According to the elemental analysis, the Cu content was 16.55% (theoretical: 16.58%) and the O content was 11.88% (theoretical: 11.88%).

Using a solution comprising the synthesized copper(I) votms·hfac, copper thin films were formed by a MOCVD process under the conditions as the same as those in Example 1. The thickness, the specific resistance, and the surface roughness of the film were also measured as in Example 1. The results are shown in Table 6.

TABLE 6

| Substrate Temperature | Film Deposition Rate (nm/min) | | | | | | | Specific Resistance | Surface roughness |
|---|---|---|---|---|---|---|---|---|---|
| (° C.) | 150 | 160 | 170 | 180 | 190 | 200 | 210 | (μΩcm) | (nm) |
| EXAMPLE 1 | 380 | 510 | 620 | 720 | 786 | 810 | 796 | 1.6 to 1.8 | 0.99 to 1.02 |
| EXAMPLE 2 | 400 | 500 | 600 | 750 | 800 | 820 | 800 | | |

Table 6 shows that the deposition rate of the copper thin film is in a range of approximately 500 nm/min to approximately 800 n/min when the substrate temperature is in a range of 160° C. to 210° C. in Examples 1 and 2. In particular, the deposition rate of the copper thin film is increased at a temperature in a range of 180° C. to 200° C., 720 nm to 820 nm of the film is deposited for 1 minute. In Examples 1 and 2, the specific resistance of the film is in a range of 1.6 to 1.8 μΩcm relative to a theoretical value of 1.6 μΩcm, and the surface roughness is in a range of 0.99 to 1.02 nm, regardless of the substrate temperature.

COMPARATIVE EXAMPLE 1

A copper thin film was prepared by a MOCVD process using a stock solution of copper(I) atms·hfac as in Example 1, except that the substrate temperature was 180° C. The thickness, the specific resistance, and the surface roughness of the film were measured as in Example 1. These results are shown In Table 7.

COMPARATIVE EXAMPLE 2

A copper thin film was prepared by a MOCVD process using a stock solution of copper(I) tmvs·hfac as in Example 1, except that the substrate temperature was 180° C. The thickness, the specific resistance, and the surface roughness of the film were measured as in Example 1. These results are shown in Table 7.

TABLE 7

|  | Film Deposition Rate (nm/min) | (Substrate Temperature: 180° C.) Specific Resistance ($\mu\Omega$cm) | Surface Roughness (nm) |
|---|---|---|---|
| COMPARATIVE EXAMPLE 1 | 30 | 2.2 | 1.5 |
| COMPARATIVE EXAMPLE 2 | 20 | 2.4 | 1.6 |

COMPARATIVE EVALUATION 1

Table 7 shows that the thicknesses of the films deposited in Comparative Examples 1 and 2 are 30 nm and 20 nm, respectively, which are significantly smaller than those in Examples 1 and 2. The resistances of these films are 2.2 $\mu\Omega$cm and 2.4 $\mu\Omega$cm which significantly deviate from the theoretical value 1.6 $\mu\Omega$cm. The surface roughnesses are 1.5 nm and 2.5 nm on average, which are significantly higher than those in Examples 1 and 2.

EXAMPLES 3 to 32

Thirty types of copper(I) complexes in which the β-diketone compound is hexafluoroacetylacetone and the unsaturated hydrocarbon moieties (Nos. 1 to 30) had alkenyl groups and silyloxy groups shown in Table 1 were synthesized and identified as in Example 1. The resulting compounds were identified as the compounds shown in Table 1.

EXAMPLES 33 to 72

Forty types of copper(I) complexes in which the β-diketone compound is hexafluoroacetylacetone and the unsaturated hydrocarbon moieties (Nos. 31 to 70) had alkynyl groups and silyloxy groups shown in Tables 2 and 3 were synthesized and identified as in Example 1. The resulting compounds were identified as the compounds shown in Tables 2 and 3.

EXAMPLES 73 to 102

Thirty types of copper(I) complexes in which the β-diketone compound is 1,3-dihydroxy-1,3-propanedione and the unsaturated hydrocarbon moieties (Nos. 1 to 30) had alkenyl groups and silyloxy groups shown in Table 1 were synthesized and identified as in Example 1. The resulting compounds were identified as the compounds shown in Table 1.

EXAMPLES 103 to 142

Forty types of copper(I) complexes in which the β-diketone compound is 1,3-dihydroxy-1,3-propanedione and the unsaturated hydrocarbon moieties (Nos. 31 to 70) had alkynyl groups and silyloxy groups shown in Tables 2 and 3 were synthesized and identified as in Example 1. The resulting compounds were identified as the compounds shown in Tables 2 and 3.

COMPARATIVE EVALUATION 2

Copper thin films were prepared as in Example 1 using 140 compounds in Examples 3 to 142, and the deposition rate and the specific resistance of each film were measured, and were comparable with the deposition rate and the specific resistance of each of the films in Examples 1 and 2.

EXAMPLES 143 to 172

The following examples show that a combination of the copper(I) complex of the present invention with another liquid compound facilitates the deposition of the film, that is, increases the deposition rate of the film.

Table 8 shows combinations of Compounds A' and B' and combinations of Compounds A', B', and C'. The MOCVD process was evaluated by these combinations. The results are shown in Table 8. The Compound A' primarily used was a hexafluoroacetylacetonate complex, and in the asterisked examples, 1,3-dihydroxy-1,3-propanedione was also used together with the hexafluoroacetylacetonate complex.

TABLE 8

| No. | Copper(I) Complex Compound A' of Present Invention | Compound B' (Liquid compound) | Compound C' (Auxiliary) | Molar Ratio in Mixture | | | Comparison of Deposition Rate** |
|---|---|---|---|---|---|---|---|
| | | | | A' | B' | C' | |
| 71 | No. 1 in Table 1 | Cu(I) atms · hfac | — | 1.0 | 0.2 | — | same |
| 72 | No. 1 in Table 1 | Cu(I) atms · hfac | — | 0.5 | 0.5 | — | increased |
| 73 | No. 1 in Table 1 | Cu(I) atms · hfac | — | 0.2 | 1.0 | — | increased |
| 74 | No. 1 in Table 1 | Cu(I) tmvs · hfac | — | 0.5 | 0.5 | — | increased |
| 75 | No. 1 in Table 1 | Cu(I) tmovs · hfac | — | 0.5 | 0.5 | — | increased |
| 76 | No. 2* in Table 1 | Cu(I) atms · hfac | — | 0.5 | 0.5 | — | increased |
| 77 | No. 2* in Table 1 | Cu(I) tvms · hfac | — | 0.5 | 0.5 | — | increased |
| 78 | No. 2* in Table 1 | Cu(I) tmvos · hfac | — | 0.5 | 0.5 | — | increased |
| 79 | No. 1 in Table 1 | No. 2 in Table 1 | — | 1.0 | 0.2 | — | increased |
| 80 | No. 1 in Table 1 | No. 2 in Table 1 | — | 0.2 | 1.0 | — | increased |
| 81 | No. 12 in Table 1 | Cu(I) atms · hfac | — | 0.5 | 0.5 | — | increased |
| 82 | No. 16 in Table 1 | Cu(I) tvms · hfac | — | 0.5 | 0.5 | — | increased |

TABLE 8-continued

| No. | Copper(I) Complex Compound A' of Present Invention | Compound B' (Liquid compound) | Compound C' (Auxiliary) | Molar Ratio in Mixture A' | B' | C' | Comparison of Deposition Rate** |
|---|---|---|---|---|---|---|---|
| 83 | No. 20 in Table 1 | Cu(I) tmovs · hfac | — | 0.5 | 0.5 | — | increased |
| 84 | No. 23 in Table 1 | Cu(I) atms · hfac | — | 0.5 | 0.5 | — | increased |
| 85 | No. 28 in Table 1 | Cu(I) tmvs · hfac | — | 0.5 | 0.5 | — | increased |
| 86 | No. 31* in Table 1 | Cu(I) atms · hfac | — | 0.5 | 0.5 | — | increased |
| 87 | No. 36* in Table 1 | Cu(I) atms · hfac | — | 0.5 | 0.5 | — | increased |
| 88 | No. 47* in Table 1 | Cu(I) atms · hfac | — | 0.5 | 0.5 | — | increased |
| 89 | No. 54* in Table 1 | Cu(I) atms · hfac | — | 0.5 | 0.5 | — | increased |
| 90 | No. 66* in Table 1 | Cu(I) atms · hfac | — | 0.5 | 0.5 | — | increased |
| 91 | No. 1 in Table 1 | No. 61 in Table 1 | — | 0.5 | 0.5 | — | increased |
| 92 | No. 2 in Table 1 | No. 70 in Table 1 | — | 0.5 | 0.5 | — | increased |
| 93 | No. 1* in Table 1 | Cu(I) atms · hfac | atms | 0.5 | 0.5 | 0.2 | increased |
| 94 | No. 1* in Table 1 | Cu(I) tmvs · hfac | tmvs | 0.5 | 0.5 | 0.2 | increased |
| 95 | No. 1* in Table 1 | Cu(I) tmovs · hfac | atms | 0.5 | 0.5 | 0.2 | increased |
| 96 | No. 1 in Table 1 | No. 2 in Table 1 | atms | 0.5 | 0.5 | 0.2 | increased |
| 97 | No. 14 in Table 1 | Cu(I) tmvs · hfac | atms | 0.5 | 0.5 | 0.2 | increased |
| 98 | No. 27 in Table 1 | Cu(I) tmvs · hfac | tmvs | 0.5 | 0.5 | 0.2 | increased |
| 99 | No. 31 in Table 1 | Cu(I) tmvs · hfac | tmvs | 0.5 | 0.5 | 0.2 | increased |
| 100 | No. 47 in Table 1 | Cu(I) tmvs · hfac | tmvs | 0.5 | 0.5 | 0.2 | increased |

**("increased": The deposition rate was increased compared to single use of A' or B'.)
("same": The deposition rate was the same as that in single use of A' or B'.)

EXAMPLE 201

The organic copper compound 201 shown in Table 4 was prepared as a stock solution forming a copper thin film. The organic copper compound was synthesized as follows.

Into 13.0 grams of copper(I) oxide, 150 ml of dried methylene chloride thoroughly deaerated using nitrogen was poured to form a suspension. While vigorously stirring the suspensionion, 6.92 g of allyltrimethoxysilane (atmos) was added to the suspension, and then 12.6 g of 1,1,1,5,5,5-hexafluoro-2,4-pentanedione was added dropwise to the suspension from a dropping funnel. The solution was stirred for 4 hours and was filtered in a nitrogen stream. The filtrate was evaporated at 35° C. under a reduced pressure to obtain a deep green liquid. The liquid was purified by column chromatography to obtain 16.7 g of a pale yellowish liquid organic copper compound, that is, copper(I) allyltrimethoxysilane 1,1,1,5,5,5-hexafluoro-2,4-pentanedionate (copper (I) atms·hfac). The resulting organic copper compound was identified by NMR and elemental analysis.

In $^1$H-NMR (CDCl$_3$), peaks were observed at δ of 0.1 (s, 9H), 1.62 (d, 2H, J=7.82 Hz), 4.62 (m, 2H), and 5.61 (m, 1H). According to the elemental analysis, the C content was 32.6% (theoretical: 32.7%), the H content was 3.51% (theoretical 3.5%), the F content was 28.3% (theoretical 28.2%), the Cu content was 15.6% (theoretical: 15.7%), and the O content was 19.7% (theoretical: 19.8%).

After the resulting stock solution was stored in a sealed container for 3 months, the solution was used for forming a copper thin film by a MOCVD process. Using a silicon substrate provided with a TiN film with a thickness of 50 nm which was formed by a sputterring process on a SiO$_2$ film with a thickness of 5,000 Å on the substrate, the substrate temperature was changed to seven levels of 150° C., 160° C., 170° C., 180° C., 190° C., 200° C., and 210° C. The evaporation temperature was set at 70° C. and the pressure was set at 2 torr. Ar gas was used as a carrier gas and the flow rate was 100 sccm.

The stock solution for forming the copper thin film was supplied for 5 minutes at a rate of 0.2 cc/min., and the film thickness was observed by a cross-sectional scanning electron microscopic image. Table 9 shows the maximum film thickness per unit time. The specific resistance of the film was measured using a four-probe-type resistivity meter and the surface roughness of the film was measured by an electron-beamn surface-roughness analyzer ERA-8000 (made by Elionix Inc.). The surface roughness is defined by the difference between the topmost portion and the bottommost portion on the surface. These results are also shown in Table 9.

EXAMPLE 202

The organic copper compound 213 shown in Table 5 was prepared as a stock solution for forming a copper thin film. The organic copper compound was synthesized as follows.

Into 13.0 grams of copper(I) oxide, 150 ml of dried methylene chloride thoroughly deaerated using nitrogen was poured to form a suspension as in Example 201. While vigorously stirring the suspension, 5.84 g of butenyltrimethoxysilane was added to the suspension, and then 12.6 g of 1,1,1,5,5,5-hexafluoro-2,4-pentanedione was added dropwise to the suspension from a dropping funnel. The solution was stirred for 4 hours and was filtered in a nitrogen stream. The filtrate was evaporated at 35° C. under a reduced pressure to obtain a deep green liquid. The liquid was purified by column chromatography to obtain 13.5g of a pale yellowish liquid organic copper compound, that is, copper(I) butenyltrimethoxysilane hexafluoro-2,4-pentanedionate. The resulting organic copper compound was identified by NMR and elemental analysis.

(11)

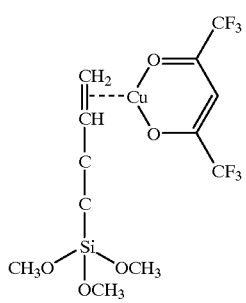

In ¹H-NMR (CDCl₃), peaks were observed at δ of 4.3 (9H), 2.4 (6H), 1.86 (2H), 1.61 (d, 2H, J=7.92 Hz), and 6.12 (s, 1H). According to the elemental analysis, the C content was 39.1% (theoretical: 39.2%), the H content was 4.82% (theoretical 4.2%), the F content was 24.8% (theoretical 24.8%), the Cu content was 13.8% (theoretical: 13.8%), and the O content was 17.3% (theoretical: 17.4%).

After the resulting stock solution was stored in a sealed container for 3 months, the solution was used for forming a copper thin film by a MOCVD process under the same conditions as those in Example 201. The thickness, the specific resistance, and the surface roughness of the film were measured as in Example 201. The results are shown in Table 9.

TABLE 9

| Substrate Temperature | Film Deposition Rate (mn/min) | | | | | | | Specific Resistance | Surface Roughness |
|---|---|---|---|---|---|---|---|---|---|
| (° C.) | 150 | 160 | 170 | 180 | 190 | 200 | 210 | (μΩcm) | (nm) |
| Example 201 | 320 | 350 | 398 | 410 | 420 | 425 | 430 | 1.5 to 1.8 | 0.96 to 0.98 |
| Example 202 | 315 | 385 | 399 | 405 | 410 | 418 | 425 | | |

Table 9 shows that the deposition rate of the copper thin film is high when the substrate temperature is in a range of 160° C. to 210° C. and particularly is approximately 400 nm/min when the substrate temperature is in a range of 180° C. to 210° C. in Examples 201 and 202. In Examples 1 and 2, the specific resistance of the film is in a range of 1.5 to 1.8 μΩcm relative to a theoretical value of 1.6 μΩcm, and the surface roughness is in a range of 0.96 to 0.98 nm, regardless of the substrate temperature.

COMPARATIVE EVALUATION 3

The film deposition rates of Comparative Examples 1 and 2 shown in Table 7 are 30 nm/min and 20 nm/min, respectively, which are significantly lower than those in Examples 201 and 202. The specific resistances of Comparative Examples 1 and 2 are 2.2 μΩcm and 2.4 μΩcm, respectively, which are significantly deviated from the theoretical value 1.6 μΩcm. The surface roughnesses of Comparative Examples 1 and 2 are 1.5 nm and 2.5 nm, respectively, on average, which are significantly higher than those in Exarnples 201 and 202.

EXAMPLES 203 to 224

Copper(I) complexes 202 to 212 (Examples 203 to 213) shown in Table 4 and 214 to 224 (Examples 204 to 224) shown in Table 5 were synthesized and identified as in Examples 201 and 202. The film deposition rate and the changes over time using these compounds were measured as in Examples 201 and 202. A copper thin film having high adhesiveness to an underlayer and satisfactory specific resistance was formed at a sufficiently high deposition rate in any compound of Examples 203 to 224.

EXAMPLES 225 to 236

Using eight types of Compounds A represented by Nos. 201, 205, 209, 213, 217, 220, 222, and 223 in Tables 4 and 5 and three types of Compound B as liquid compounds, that is, copper(I) atms·hfac, copper(I) tmvs·hfac, and copper(I) tmovs·hfac, 100 parts by weight of Compound A and 0.01 to 40 parts by weight of Compound B were thoroughly mixed to prepare 24 stock solutions for forming copper thin films as shown in Table 10. After each of the resulting stock solutions was stored in a sealed container for 3 months, the solution was used for forming a copper thin film by a MOCVD process as in Example 201, except that the substrate temperature was 180° C. Table 10 shows whether or not the deposition rate is improved by the stock solutions containing both Compound A and Compound B. The thickness, the specific resistance, and the surface roughness of the resulting copper thin-film were measured as in Example 201. The results are shown in Table 11.

COMPARATTVE EXAMPLERS 3 to 14

Using the three Compounds B in Examples 225 to 236, 100 parts by weight of Compound A and less than 0.01 parts by weight or more than 40 parts by weight of Compound B were homogeneously mixed to prepare 24 stock solutions for forming copper thin films as shown in Table 10. Whether or not the film deposition rate was improved was determined as in Example 201. The results are shown in Table 10. The thickness, the specific resistance, and the surface roughness of each copper thin film were measured as in Example 201. The results are shown in Table 11.

TABLE 10

| | Compound A | Compound B (Liquid compound) | Compound C (Auxiliary) | Weight % B | C | Comparison of Deposition Rate** |
|---|---|---|---|---|---|---|
| EXAMPLES | | | | | | |
| 225 | No. 201 in Table 4 | Cu(I) atms · hfac | — | 0.01 | — | increased |
| 226 | No. 201 in Table 4 | Cu(I) tmvs · hfac | — | 0.5 | — | increased |
| 227 | No. 201 in Table 4 | Cu(I) tmovs · hfac | — | 0.01 | — | increased |
| 228 | No. 205 in Table 4 | Cu(I) atms · hfac | — | 1.0 | — | increased |
| 229 | No. 205 in Table 4 | Cu(I) tmvs · hfac | — | 0.2 | — | increased |
| 230 | No. 209 in Table 4 | Cu(I) atms · hfac | — | 1.0 | — | increased |
| 231 | No. 209 in Table 4 | Cu(I) atms · hfac | — | 5.0 | — | same |
| 232 | No. 213 in Table 5 | Cu(I) atms · hfac | — | 8.0 | — | same |
| 233 | No. 217 in Table 5 | Cu(I) atms · hfac | — | 9.0 | — | increased |
| 234 | No. 220 in Table 5 | Cu(I) atms · hfac | — | 15.0 | — | increased |
| 235 | No. 222 in Table 5 | Cu(I) atms · hfac | — | 20.0 | — | increased |
| 236 | No. 223 in Table 5 | Cu(I) atms · hfac | — | 0.1 | — | increased |
| COMPARATIVE EXAMPLES | | | | | | |
| 3 | No. 201 in Table 4 | Cu(I) atms · hfac | — | 0.001 | — | decreased |
| 4 | No. 201 in Table 4 | Cu(I) tmvs · hfac | — | 0.001 | — | decreased |
| 5 | No. 201 in Table 4 | Cu(I) tmovs · hfac | — | 0.001 | — | decreased |
| 6 | No. 205 in Table 4 | Cu(I) atms · hfac | — | 0.001 | — | decreased |
| 7 | No. 205 in Table 4 | Cu(I) tmvs · hfac | — | 0.001 | — | decreased |
| 8 | No. 209 in Table 4 | Cu(I) atms · hfac | — | 0.001 | — | decreased |
| 9 | No. 209 in Table 4 | Cu(I) atms · hfac | — | 50.0 | — | decreased |
| 10 | No. 213 in Table 5 | Cu(I) atms · hfac | — | 40.0 | — | decreased |
| 11 | No. 217 in Table 5 | Cu(I) atms · hfac | — | 30.0 | — | decreased |
| 12 | No. 220 in Table 5 | Cu(I) atms · hfac | — | 60.0 | — | decreased |
| 13 | No. 222 in Table 5 | Cu(I) atms · hfac | — | 80.0 | — | decreased |
| 14 | No. 223 in Table 5 | Cu(I) atms · hfac | — | 90.0 | — | decreased |

**("increased": The deposition rate was increased compared to single use of A or B.)
("same": The deposition rate was the same as that in single use of A or B.)
("decreased": The deposition rate was decreased compared to single use of A or B.)

TABLE 11

(Substrate Temperature: 180° C.)

| | Film Deposition Rate (nm/min) | Specific Resistance ($\mu\Omega$cm) | Surface Roughness (nm) |
|---|---|---|---|
| EXAMPLE 225 | 440 | 1.5 to 1.8 | 0.95 |
| EXAMPLE 226 | 450 | 1.5 to 1.8 | 0.93 |
| EXAMPLE 227 | 460 | 1.5 to 1.8 | 0.96 |
| EXAMPLE 228 | 480 | 1.5 to 1.8 | 0.96 |
| EXAMPLE 229 | 440 | 1.5 to 1.8 | 0.92 |
| EXAMPLE 230 | 460 | 1.5 to 1.8 | 0.95 |
| EXAMPLE 231 | 490 | 1.5 to 1.8 | 0.96 |
| EXAMPLE 232 | 520 | 1.5 to 1.8 | 0.97 |
| EXAMPLE 233 | 440 | 1.5 to 1.8 | 0.94 |
| EXAMPLE 234 | 480 | 1.5 to 1.8 | 0.95 |
| EXAMPLE 235 | 520 | 1.5 to 1.8 | 0.96 |
| EXAMPLE 236 | 560 | 1.5 to 1.8 | 0.96 |
| COMPARATIVE EXAMPLE 3 | 240 | 2.7 to 3.0 | 0.51 |
| COMPARATIVE EXAMPLE 4 | 220 | 2.7 to 3.0 | 0.60 |
| COMPARATIVE EXAMPLE 5 | 210 | 2.7 to 3.0 | 0.41 |
| COMPARATIVE EXAMPLE 6 | 200 | 2.7 to 3.0 | 0.22 |
| COMPARATIVE EXAMPLE 7 | 215 | 2.7 to 3.0 | 1.46 |
| COMPARATIVE EXAMPLE 8 | 218 | 2.7 to 3.0 | 1.77 |
| COMPARATIVE EXAMPLE 9 | 210 | 2.7 to 3.0 | 2.01 |
| COMPARATIVE EXAMPLE 10 | 230 | 2.7 to 3.0 | 1.71 |
| COMPARATIVE EXAMPLE 11 | 241 | 2.7 to 3.0 | 1.59 |
| COMPARATIVE EXAMPLE 12 | 230 | 2.7 to 3.0 | 1.50 |
| COMPARATIVE EXAMPLE 13 | 242 | 2.7 to 3.0 | 0.41 |
| COMPARATIVE EXAMPLE 14 | 238 | 2.7 to 3.0 | 0.49 |

Table 11 shows that the deposition rate is as high as 440 nm to 560 nm/min when the content of Compound B (liquid compound) is in a range of 0.01 to 40 percent by weight, but is on the order of 200 nm when the content is outside this range. The specific resistance is in a range of 1.5 to 1.8 $\mu\Omega$cm relative to the theoretical value of 1.6 $\mu\Omega$cm and the surface roughness is 0.95 nm on average when the content of Compound B is in a range of 0.01 to 40 percent by weight. In contrast, the specific resistance of the film is 2.7 to 3.0 $\mu\Omega$cm and the surface roughness is 1.06 nm on average when the content of Compound B (liquid compound) is outside this range.

EXAMPLES 237 to 246

Using five types of Compounds A represented by Nos. 201, 205, 213, 217, and 220 in Tables 4 and 5, three types of Compound B as liquid compounds, that is, copper(I) atms·hfac, copper(I) tmvs·hfac, and copper(I) tmovs·hfac, and four Compounds C as auxiliary components, that is, atms, atmos, tmvs, and tmovs, Compounds A, B, and C were thoroughly mixed according to the formulations shown in Table 12 to prepare 10 stock solutions for forming copper thin films. In Examples 237 to 246, 0.01 to 40 parts by weight of Compound B was added to 100 parts by weight of Compound A, and 0.01 to 40 parts by weight of Compound C was added to 100 parts by weight of Compound B. After each of the resulting stock solutions was stored in a sealed container for 3 months, the solution was used for forming a copper thin film by a MOCVD process as in Example 201, except that the substrate temperature was 180° C. Table 10 shows whether or not the deposition rate is improved by the stock solutions containing Compounds A, B, and C The thickness, the specific resistance, and the surface roughness of the resulting copper thin film were measured as in Example 201. The results are shown in Table 13.

COMPARATIVE EXAMPLES 15 to 24

Using the three Compounds B (liquid compounds) and the four Compounds C (auxiliary components) in Examples 237 to 246, less than 0.01 parts by weight or more than 40 parts by weight of Compound B with respect to 100 parts by weight of Compound A and less than 0.01 parts by weight or more than 40 parts by weight of Compound C with respect to 100 parts by weight of Compound B were homogeneously mixed with Compound A to prepare to stock solutions for forming copper thin films as shown in Table 12. Whether or not the film deposition rate was improved was determined as in Example 201. The results are shown in Table 13. The thickness, the specific resistance, and the surface roughness of each copper thin film were measured as in Example 201. The results are shown in Table 13.

TABLE 12

|  | Compound A | Compound B (Liquid compound) | Compound C (Auxiliary) | Weight % B | Weight % C | Comparison of Deposition Rate** |
|---|---|---|---|---|---|---|
| EXAMPLES | | | | | | |
| 237 | No. 201 in Table 4 | Cu(I) atms · hfac | atms | 0.01 | 1.0 | increased |
| 238 | No. 201 in Table 4 | Cu(I) atms · hfac | atmos | 0.2 | 0.1 | increased |
| 239 | No. 201 in Table 4 | Cu(I) atms · hfac | tmvs | 1.0 | 2.0 | increased |
| 240 | No. 201 in Table 4 | Cu(I) atms · hfac | tmovs | 2.0 | 5.0 | same |
| 241 | No. 205 in Table 4 | Cu(I) tmovs · hfac | atms | 5.0 | 10.0 | increased |
| 242 | No. 205 in Table 4 | Cu(I) tmovs · hfac | tmovs | 10.0 | 20.0 | increased |
| 243 | No. 213 in Table 5 | Cu(I) tmvs · hfac | atms | 20.0 | 0.01 | increased |
| 244 | No. 213 in Table 5 | Cu(I) tmvs · hfac | tmvs | 30.0 | 0.5 | increased |
| 245 | No. 217 in Table 5 | Cu(I) tmvs · hfac | tmvs | 40.0 | 40.0 | same |
| 246 | No. 220 in Table 5 | Cu(I) tmvs · hfac | tmvs | 0.01 | 5.0 | increased |
| COMPARATIVE EXAMPLES | | | | | | |
| 15 | No. 201 in Table 4 | Cu(I) atms · hfac | atms | 0.01 | 1.0 | decreased |
| 16 | No. 201 in Table 4 | Cu(I) atms · hfac | atmos | 0.2 | 0.1 | decreased |
| 17 | No. 201 in Table 4 | Cu(I) atms · hfac | tmvs | 1.0 | 2.0 | decreased |
| 18 | No. 201 in Table 4 | Cu(I) atms · hfac | tmovs | 2.0 | 5.0 | decreased |
| 19 | No. 205 in Table 4 | Cu(I) tmovs · hfac | atms | 5.0 | 10.0 | decreased |
| 20 | No. 205 in Table 4 | Cu(I) tmovs · hfac | tmovs | 10.0 | 20.0 | decreased |
| 21 | No. 213 in Table 5 | Cu(I) tmvs · hfac | atms | 20.0 | 0.01 | decreased |
| 22 | No. 213 in Table 5 | Cu(I) tmvs · hfac | tmvs | 30.0 | 0.5 | decreased |
| 23 | No. 217 in Table 5 | Cu(I) tmvs · hfac | tmvs | 40.0 | 40.0 | decreased |
| 24 | No. 220 in Table 5 | Cu(I) tmvs · hfac | tmvs | 0.01 | 5.0 | decreased |

**("increased": The deposition rate was increased compared to single use of A or B.)
("same": The deposition rate was the same as that in single use of A or B.)
("decreased": The deposition rate was decreased compared to single use of A or B.)

TABLE 13

| | (Substrate Temperature: 180° C.) | | |
|---|---|---|---|
| | Film Deposition Rate (nm/min) | Specific Resistance (μΩcm) | Surface Roughness (nm) |
| EXAMPLE 237 | 460 | 1.5 to 1.8 | 0.94 |
| EXAMPLE 238 | 510 | 1.5 to 1.8 | 0.92 |
| EXAMPLE 239 | 560 | 1.5 to 1.8 | 0.95 |
| EXAMPLE 240 | 600 | 1.5 to 1.8 | 0.95 |
| EXAMPLE 241 | 460 | 1.5 to 1.8 | 0.91 |
| EXAMPLE 242 | 560 | 1.5 to 1.8 | 0.94 |
| EXAMPLE 243 | 650 | 1.5 to 1.8 | 0.95 |
| EXAMPLE 244 | 650 | 1.5 to 1.8 | 0.96 |
| EXAMPLE 245 | 680 | 1.5 to 1.8 | 0.94 |
| EXAMPLE 246 | 710 | 1.5 to 1.8 | 0.94 |
| COMPARATIVE EXAMPLE 15 | 310 | 2.6 to 2.8 | 1.31 |
| COMPARATIVE EXAMPLE 16 | 315 | 2.6 to 2.8 | 1.41 |
| COMPARATIVE EXAMPLE 17 | 310 | 2.6 to 2.8 | 1.48 |
| COMPARATIVE EXAMPLE 18 | 318 | 2.6 to 2.8 | 1.42 |
| COMPARATIVE EXAMPLE 19 | 320 | 2.6 to 2.8 | 1.71 |
| COMPARATIVE EXAMPLE 20 | 318 | 2.6 to 2.8 | 1.79 |
| COMPARATIVE EXAMPLE 21 | 323 | 2.6 to 2.8 | 1.68 |
| COMPARATIVE EXAMPLE 22 | 338 | 2.6 to 2.8 | 1.52 |
| COMPARATIVE EXAMPLE 23 | 340 | 2.6 to 2.8 | 1.41 |
| COMPARATIVE EXAMPLE 24 | 323 | 2.6 to 2.8 | 1.69 |

Table 12 shows that the deposition rate is as high as 460 nm to 710 nm/min when the content of Compound C (auxiliary component) is in a range of 0.01 to 40 percent by weight, but is on the order of 300 nm when the content is less than 0.01 percent by weight or more than 40 percent by weight. The specific resistance is in a range of 1.5 to 1.8 $\mu\Omega$cm relative to the theoretical value of 1.6 $\mu\Omega$cm and the surface roughness is 0.94 nm on average when the content of Compound C (auxiliary component) is in a range of 0.01 to 40 percent by weight. In contrast, the specific resistance of the film is 2.6 to 2.8 $\mu\Omega$cm and the surface roughness is 1.54 nm on average when the content of Compound C (auxiliary component) is outside this range.

As described above, in the first to third aspects of the present invention, a stock solution containing only an organic copper compound is used for forming a copper thin film by a MOCVD process. Thus, the film deposition rate is further improved and the copper thin film has high adhesiveness to an underlayer. Moreover, the organic copper compound prior to the film deposition is resistant to decomposition and has a prolonged life.

In the fourth and fifth aspects of the present invention, another organic copper compound containing monovalent copper, such as copper(I) atms·hfac, copper(I) tmvs·hfac, or copper(I) tmovs·hfac is added to the above organic copper compound of the present invention. Thus, the organic copper compound can be readily decomposed in an initial deposition stage, and the deposition of copper on the underlayer is facilitated. As a result, the deposition rate of the copper thin film is increased.

In the sixth aspect of the present invention, at least one compound selected from atms, atmos, tmvs, and tmovs is added to the mixed organic copper compound solution. The proportion of carbon double bonds is increased in the solution, and the π bonding of the copper atom is enhanced. Since the decomposition of the organic copper compound is suppressed in a stock solution, the stock solution has a prolonged storage life.

A copper thin film formed using the above organic copper compound by a MOCVD has high purity and resistance which is substantially equal to the theoretical value of pure copper, has high adhesiveness to an underlayer, and has a small surface roughness. The copper thin film can be effectively used for embedding deep contact holes for copper multilayer interconnection.

The disclosures of the priority documents, JP Hei 11-355988, filed in Japan on Dec. 15, 1999; JP 2000-118258, filed in Japan on Apr. 19, 2000; JP 2000-203310, filed in Japan on Jul. 5, 2000; JP 2000-248453, filed in Japan on Aug. 18, 2000; and JP 2000-302405, filed in Japan on Oct. 2, 2000, are incorporated by reference herein in their entireties.

What is claimed is:

1. An organic copper compound represented by the following formula (1):

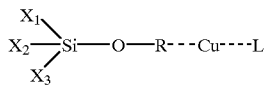

(1)

wherein L is a β-diketone compound; R is an unsaturated hydrocarbon moiety; Cu is monovalent copper coordinated with the L and the R; $X_1$, $X_2$, and $X_3$ are each a hydrogen atom, an alkyl group having 1 to 5 carbon atoms, or an alkoxy group having 1 to 4 carbon atoms; and $X_1$, $X_2$, and $X_3$ may be the same or different from each other.

2. The organic copper compound according to claim 1, wherein R comprises either an alkenyl group or an alkyyl group.

3. The organic copper compound according to claim 2, wherein the alkenyl group is an ethenyl, propenyl, butenyl, or pentenyl group.

4. The organic copper compound according to claim 2, wherein the alkynyl group is an ethynyl, propynyl, butynyl, pentynyl, or hexynyl group.

5. The organic copper compound according to claim 1, wherein the β-diketone compound is either hexafluoroacetylacetone or 1,3-dihydroxy-1,3-propanedione.

6. The organic copper compound according to claim 2, wherein the β-diketone compound is either hexafluoroacetylacetone or 1,3-dihydroxy-1,3-propanedione.

7. The organic copper compound according to claim 3, wherein the β-diketone compound is either hexafluoroacetylacetone or 1,3dihydroxy1,3-propanedione.

8. The organic copper compound according to claim 4, wherein the β-diketone compound is either hexafluoroacetylacetone or 1,3-dihydroxy-1,3-propanedione.

9. An organic copper compound represented by the following formula (2):

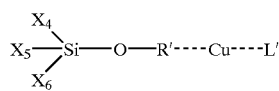

(2)

wherein L' is a hexafluoroacetylacetone; R' is an olefinic hydrocarbon moiety with 3 or more carbon atoms; Cu is monovalent copper coordinated with the L' and the R'; one or two of $X_4$, $X_5$, and $X_6$ are each an alkoxy group having 1 to 8 carbon atoms; the others of $X_4$, $X_5$, and $X_6$ are each an alkyl group having 1 to 8 carbon atoms or a hydrogen atom; and the alkoxy groups or the alkyl groups may be the same or different from each other.

10. The organic copper compound according to claim 9, wherein R' is a propenyl, butenyl, or pentenyl group.

11. An organic copper compound represented by the following formula (3):

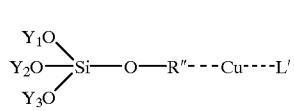

(3)

wherein L' is a hexafluoroacetylacetone; R" is an olefinic hydrocarbon moiety with 4 or more carbon atoms; Cu is monovalent copper coordinated with L' and R"; $Y_1$, $Y_2$, and $Y_3$ are each an alkoxy group having 1 to 4 carbon atoms; and $Y_1$, $Y_2$, and $Y_3$ may be the same or different from each other.

12. The organic copper compound according to claim 11, wherein the R" is a propenyl, butenyl, or pentenyl group.

13. A liquid mixture comprising
the organic copper compound of claim 1;
at least one liquid compound selected from the group consisting of trimethylvinylsilane, vinyloxytrimethylsilane, allyloxytrimethylsilane, allyltrimethylsilane, 3-hexyne, 2-butyne; and
a Cu(I) hexafluoroacetylacetonate compound.

14. A liquid mixture comprising
the organic copper compound of claim 2;
at least one liquid compound selected from the group consisting of trimethylvinylsilane, vinyloxytrimethylsilane, allyloxytrimethylsilane, allyltrimethylsilane, 3-hexyne, 2-butyne; and
a Cu(I) hexafluoroacetylacetonate compound.

15. A liquid mixture comprising
the organic copper compound of claim 3;
at least one liquid compound selected from the group consisting of trimethylvinylsilane, vinyloxytrimethylsilane, allyloxytrimethylsilane, allyltrimethylsilane, 3-hexyne, 2-butyne; and
a Cu(I) hexafluoroacetylacetonate compound.

16. A liquid mixture comprising
the organic copper compound of claim 4;
at least one liquid compound selected from the group consisting of trimethylvinylsilane, vinyloxytrimethylsilane, allyloxytrimethylsilane, allyltrimethylsilane, 3-hexyne, 2-butyne; and
a Cu(I) hexafluoroacetylacetonate compound.

17. A liquid mixture comprising
the organic copper compound of claim 5;
at least one liquid compound selected from the group consisting of trimethylvinylsilane, vinyloxytrimethylsilane, allyloxytrimethylsilane, allyltrimethylsilane, 3-hexyne, 2-butyne; and
a Cu(I) hexafluoroacetylacetonate compound.

18. A liquid mixture comprising
the organic copper compound of claim 9; and
at least one liquid compound selected from the group consisting of copper(I) allyltrimethylsilane hexafluoroacetylacetonate, copper(I) trimethylvinylsilane hexafluoroacetylacetonate, and copper(I) trimethoxyvinylsilane hexafluoroacetylacetonate.

19. A liquid mixture comprising
the organic copper compound of claim 10; and
at least one liquid compound selected from the group consisting of copper(I) allyltrimethylsilane hexafluoroacetylacetonate, copper(I) trimethylvinylsilane hexafluoroacetylacetonate, and copper(I) trimethoxyvinylsilane hexafluoroacetylacetonate.

20. A liquid mixture comprising
the organic copper compound of claim 11; and
at least one liquid compound selected from the group consisting of copper(I) allyltrimethylsilane hexafluoroacetylacetonate, copper(I) trimethylvinylsilane hexafluoroacetylacetonate, and copper(I) trimethoxyvinylsilane hexafluoroacetylacetonate.

21. A liquid mixture comprising
the organic copper compound of claim 12; and
at least one liquid compound selected from the group consisting of copper(I) allyltrimethylsilane hexafluoroacetylacetonate, copper(I) trimethylvinylsilane hexafluoroacetylacetonate, and copper(I) trimethoxyvinylsilane hexafluoroacetylacetonate.

22. A liquid mixture comprising
the organic copper compound of claim 9;
at least one compound selected from the group consisting of copper(I) allyltrimethylsilane hexafluoroacetylacetonate, copper(I) trimethylvinylsilane hexafluoroacetylacetonate, and copper(I) trimethoxyvinylsilane hexafluoroacetylacetonate; and
at least one compound selected from the group consisting of allyltrimethylsilane, allyltrimethoxysilane, trimethylvinylsilane, and trimethoxyvinylsilane.

23. A liquid mixture comprising
the organic copper compound of claim 10;
at least one compound selected from the group consisting of copper(I) allyltrimethylsilane hexafluoroacetylacetonate, copper(I) trimethylvinylsilane hexafluoroacetylacetonate, and copper(I) trimethoxyvinylsilane hexafluoroacetylacetonate; and
at least one compound selected from the group consisting of allyltrimethylsilane, allyltrimethoxysilane, trimethylvinylsilane, and trimethoxyvinylsilane.

24. A liquid mixture comprising
the organic copper compound of claim 11;
at least one compound selected from the group consisting of copper(I) allyltrimethylsilane hexafluoroacetylacetonate, copper(I) trimethylvinylsilane hexafluoroacetylacetonate, and copper(I) trimethoxyvinylsilane hexafluoroacetylacetonate; and
at least one compound selected from the group consisting of allyltrimethylsilane, allyltrimethoxysilane, trimethylvinylsilane, and trimethoxyvinylsilane.

25. A liquid mixture comprising
the organic copper compound of claim 12;
at least one compound selected from the group consisting of copper(I) allyltrimethylsilane hexafluoroacetylacetonate, copper(I) trimethylvinylsilane hexafluoroacetylacetonate, and copper(I) trimethoxyvinylsilane hexafluoroacetylacetonate; and
at least one compound selected from the group consisting of allyltrimethylsilane, allyltrimethoxysilane, trimethylvinylsilane, and trimethoxyvinylsilane.

26. A copper film prepared by a metal organic chemical vapor deposition process using the organic copper compound of claim 1.

27. A copper film prepared by a metal organic chemical vapor deposition process using the organic copper compound of claim 2.

28. A copper film prepared by a metal organic chemical vapor deposition process using the organic copper compound of claim 3.

29. A copper film prepared by a metal organic chemical vapor deposition process using the organic copper compound of claim 4.

30. A copper film prepared by a metal organic chemical vapor deposition process using the organic copper compound of claim 5.

31. A copper film prepared by a metal organic chemical vapor deposition process using the organic copper compound of claim 9.

32. A copper film prepared by a metal organic chemical vapor deposition process using the organic copper compound of claim 10.

33. A copper film prepared by a metal organic chemical vapor deposition process using the organic copper compound of claim 11.

34. A copper film prepared by a metal organic chemical vapor deposition process using the organic copper compound of claim 12.

35. A copper film prepared by a metal organic chemical vapor deposition process using the liquid mixture of claim 13.

36. A copper film prepared by a metal organic chemical vapor deposition process using the liquid mixture of claim 14.

37. A copper film prepared by a metal organic chemical vapor deposition process using the liquid mixture of claim 15.

38. A copper film prepared by a metal organic chemical vapor deposition process using the liquid mixture of claim 16.

39. A copper film prepared by a metal organic chemical vapor deposition process using the liquid mixture of claim 17.

40. A copper film prepared by a metal organic chemical vapor deposition process using the liquid mixture of claim 18.

41. A copper film prepared by a metal organic chemical vapor deposition process using the liquid mixture of claim 19.

42. A copper film prepared by a metal organic chemical vapor deposition process using the liquid mixture of claim 20.

43. A copper film prepared by a metal organic chemical vapor deposition process using the liquid mixture of claim 21.

44. A copper film prepared by a metal organic chemical vapor deposition process using the liquid mixture of claim 22.

45. A copper film prepared by a metal organic chemical vapor deposition process using the liquid mixture of claim 23.

46. A copper film prepared by a metal organic chemica vapor deposition process using the liquid mixture of claim 24.

47. A copper film prepared by a metal organic chemical vapor deposition process using the liquid mixture of claim 25.

48. A method of making an organic copper compound, the method comprising coordinating a β-diketone compound and an unsaturated hydrocarbon moiety with monovalent copper; and forming the organic copper compound of claim 1.

49. A method of making an organic copper compound, the method comprising coordinating a hexafluoroacetylacetone and an olefinic hydrocarbon moiety with monovalent copper; and forming the organic copper compound of claim 9.

50. A method of making an organic copper compound, the method comprising coordinating a hexafluoroacetylacetone and an olefinic hydrocarbon moiety with monovalent copper; and forming the organic copper compound of claim 11.

51. A method of making a liquid mixture, the method comprising mixing a Cu(I) hexafluoroacetylacetonate compound and at least one liquid compound selected from the group consisting of trimethylvinylsilane, vinyloxytrimethylsilane, allyloxytrimethylsilane, allyltrimethylsilane, 3-hexyne, and 2-butyne; and forming the liquid mixture of claim 13.

52. A method of making a liquid mixture, the method comprising mixing an organic copper compound with at least one liquid compound selected from the group consisting of copper(I) allyltrimethylsilane hexafluoroacetylacetonate, copper(I) trimethylvinylsilane hexafluoroacetylacetonate, and copper(I) trimethoxyvinylsilane hexafluoroacetylacetonate; and forming the liquid mixture of claim 18.

53. A method of making a liquid mixture, the method comprising mixing an organic copper compound with at least one liquid compound selected from the group consisting of copper(I) allyltfimethylsilane hexafluoroacetylacetonate, copper(I) trimethylvinylsilane hexafluoroacetylacetonate, and copper(I) trimethoxyvinylsilane hexafiuoroacetylacetonate; and forming the liquid mixture of claim 20.

54. A method of making a liquid mixture, the method comprising mixing an organic copper compound with at least one compound selected from the group consisting of allyltrimethylsilane, allyltrimethoxysilane, trimethylvinylsilane, and trimethoxyvinylsilane; and forming the liquid mixture of claim 22.

55. A method of making a liquid mixture, the method comprising mixing an organic copper compound with at least one compound selected from the group consisting of allyltrimethylsilane, allyltrimethoxysilane, trimethylvinylsilane, and trimethoxyvinylsilane; and forming the liquid mixture of claim 24.

56. A method of making a copper film, the method comprising depositing a copper film by a metal organic chemical vapor deposition process; and forming the copper film of claim 26.

57. A method of making a copper film, the method comprising depositing a copper film by a metal organic chemical vapor deposition process; and forming the copper film of claim 31.

58. A method of making a copper film, the method comprising depositing a copper film by a metal organic chemical vapor deposition process; and forming the copper film of claim 33.

59. A method of making a copper film, the method comprising depositing a copper film by a metal organic chemical vapor deposition process; and forming the copper film of claim 40.

60. A method of making a copper film, the method comprising depositing a copper film by a metal organic chemical vapor deposition process; and forming the copper film of claim 42.

61. A method of making a copper film, the method comprising depositing a copper film by a metal organic chemical vapor deposition process; and forming the copper film of claim 44.

62. A method of making a copper film, the method comprising dosiing a copper film by a metal organic chemical vapor deposition process; and forming the copper film of claim 46.

* * * * *